United States Patent [19]

Böhner

[11] Patent Number: 4,515,620

[45] Date of Patent: May 7, 1985

[54] TRIAZA COMPOUNDS

[75] Inventor: Beat Böhner, Binningen, Switzerland

[73] Assignee: Ciba Geigy Corporation, Ardsley, N.Y.

[21] Appl. No.: 454,950

[22] Filed: Jan. 3, 1983

[30] Foreign Application Priority Data

Jan. 12, 1982 [CH] Switzerland ............. 153/82

[51] Int. Cl.³ ............... C07D 239/46; C07D 251/42; C07D 239/47; A61K 47/36
[52] U.S. Cl. ............................ 71/91; 71/92; 544/197; 544/198; 544/208; 544/209; 544/211; 544/212; 544/321; 544/323; 544/324; 544/331; 544/332
[58] Field of Search ............... 544/321, 332, 323, 324, 544/331, 197, 198, 208, 209, 211, 212; 71/91, 92

[56] References Cited

U.S. PATENT DOCUMENTS 3,242,174  3/1966  McManus ..................... 544/159
4,191,553  3/1980  Reap ............................ 71/92

FOREIGN PATENT DOCUMENTS 1226106  10/1966  Fed. Rep. of Germany ......... 71/92
3243533   6/1983  Fed. Rep. of Germany ...... 544/319
58-15962  1/1983  Japan ............................ 544/319

Primary Examiner—Robert Gerstl
Attorney, Agent, or Firm—Edward McC. Roberts; Frederick H. Rabin; Bruce M. Collins

[57] ABSTRACT

Triaza compounds of the general formula I

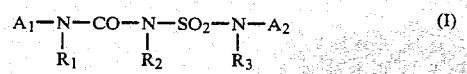

and their basic addition salts have good selective herbicidal and plant growth regulating properties when applied pre- and postemergence. In the formula, each of $A_1$ and $A_2$ is a homocyclic or heterocyclic aromatic radical such as phenyl, naphthyl, indanyl, imidazolyl, pyridinyl, pyrimidinyl, pyrazolyl or triazolyl, each of which is unsubstituted or mono- to trisubstituted, while only one of $A_1$ and $A_2$ may be a phenyl, naphthyl or indanyl radical, and each of $R_1$ and $R_3$ is hydrogen or $C_1$–$C_4$ alkyl and $R_2$ is hydrogen or a cation.

11 Claims, No Drawings

TRIAZA COMPOUNDS

The present invention relates to novel triaza compounds, to a process for their preparation, to compositions which contain these novel compounds, and to the use of these compounds or of compositions containing them for regulating plant growth or for controlling unwanted plant growth.

The novel triaza compounds have the formula I

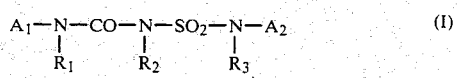

wherein each of $A_1$ and $A_2$ is a homocyclic or heterocyclic aromatic radical which may be unsubstituted or mono- to trisubstituted by halogen, cyano, $C_1$–$C_3$alkyl, $C_1$–$C_3$haloalkyl, $C_1$–$C_3$alkoxy, $C_1$–$C_3$haloalkoxy, $C_1$–$C_3$alkylthio, $C_1$–$C_3$haloalkylthio, sulfamoyl, $C_1$–$C_3$alkylsulfonyl, $C_1$–$C_3$alkylsulfoxyl, $C_1$–$C_3$alkoxycarbonyl, $C_1$–$C_3$alkylcarbonyl, amino, $C_1$–$C_3$alkylamino, di($C_1$–$C_3$alkyl)amino, nitro and/or thiocyanato; $R_1$ and $R_3$ are each independently hydrogen or $C_1$–$C_4$alkyl; and $R_2$ is hydrogen or the cation of an alkali metal or alkaline earth metal or the cation of a quaternary ammonium base, with the proviso that at least one of $A_1$ and $A_2$ is an unsubstituted or substituted heterocyclic radical.

Homocyclic or heterocyclic aromatic radicals will be understood as meaning e.g. the aromatic radicals naphthyl and phenyl as well as the aromatic 5- to 6-membered heterocycles furane, thiophene, pyrrole, imidazole, pyrane, pyridine, pyrimidine, pyrazole and triazine.

Accordingly, the triaza compounds of the formula I may also be defined as follows: $A_1$ and $A_2$ are radicals selected from the group consisting of phenyl, naphthyl, indanyl, imidazolyl, pyridinyl, pyrimidinyl, pyrazolyl and triazinyl, each of which is unsubstituted or mono- to trisubstituted by halogen, cyano, $C_1$–$C_3$alkyl, $C_1$–$C_3$haloalkyl, $C_1$–$C_3$alkoxy, $C_1$–$C_3$haloalkoxy, $C_1$–$C_3$alkylthio, $C_1$–$C_3$haloalkylthio, $C_1$–$C_3$alkylsulfonyl, $C_1$–$C_3$alkylsulfoxy, $C_1$–$C_3$alkoxycarbonyl, $C_1$–$C_3$alkylcarbonyl, amino, $C_1$–$C_3$alkylamino, di($C_1$–$C_3$alkyl)amino, nitro and/or thiocyanato, and $R_1$, $R_2$ and $R_3$ are as defined above.

Urea, triazine and pyrimidine compounds with herbicidal properties are generally known. Similar N-heterocycloaminocarbonylarylsulfamates with herbicidal and plant growth regulating properties have recently been described in U.S. Pat. No. 4,191,553.

In the above definitions, alkyl is straight chain or branched alkyl, e.g. methyl, ethyl, n-propyl or isopropyl. Alkoxy is methoxy, ethoxy, n-propoxy and isopropoxy, with methoxy, ethoxy or isopropoxy being preferred.

Alkylthio may be methylthio, ethylthio, n-propylthio and isopropylthio, with methylthio and ethylthio being preferred.

Alkylsulfonyl may be methylsulfonyl, ethylsulfonyl, n-propylsulfonyl and isopropylsulfonyl, with methylsulfonyl and ethylsulfonyl being preferred.

Alkylsulfoxyl may be methylsulfoxyl, ethylsulfoxyl, n-propylsulfoxyl and isopropylsulfoxyl, with methylsulfoxyl and ethylsulfoxyl being preferred.

Halogen by itself and as moiety of haloalkyl, haloalkoxy and haloalkylthio is fluorine, chlorine and bromine, with fluorine and chlorine being preferred. Accordingly, haloalkyl by itself or as moiety of another substituent may be: chloromethyl, dichloromethyl, trichloromethyl, difluoromethyl, trifluoromethyl, 2-chloroethyl, 1,1,2,2-tetrachloroethyl, 2,2,2-trifluoroethyl, perfluoroethyl, 1,1,2,2-tetrafluoroethyl, 1,1,2-trifluoro-2-chloroethyl etc., and is preferably chloromethyl, difluoromethyl and trifluoromethyl.

The invention also relates to the salts which the compounds of the formula I are able to form with amines, alkali metal bases and alkaline earth metal bases or with quaternary ammonium bases.

Preferred alkali metal hydroxides and alkaline earth metal hydroxides as salt formers are the hydroxides of lithium, sodium, magnesium or calcium, with sodium or potassium hydroxide being particularly preferred.

Examples of quaternary ammonium bases are in general the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Preferred compounds of the formula I are those in which $A_1$ is a phenyl, naphthyl, thiophenyl, furanyl or pyridinyl radical; $A_2$ is a pyrimidinyl radical or a symmetrical or asymmetrical triazinyl radical which is unsubstituted or mono- to trisubstituted by halogen, cyano, $C_1$–$C_3$alkyl, $C_1$–$C_3$haloalkyl, $C_1$–$C_3$alkoxy, $C_1$–$C_3$haloalkoxy, $C_1$–$C_3$alkylthio, $C_1$–$C_3$haloalkylthio, sulfamoyl, $C_1$–$C_3$alkylsulfonyl, $C_1$–$C_3$alkylsulfoxyl, $C_1$–$C_3$alkoxycarbonyl, $C_1$–$C_3$alkylcarbonyl, amino, $C_1$–$C_3$alkylamino, di($C_1$–$C_3$alkyl)amino, nitro and/or thiocyanato; each of $R_1$ and $R_3$ is hydrogen; and $R_2$ is hydrogen or the cation of an alkali metal or alkaline earth metal or the cation of a quaternary ammonium group.

Particularly preferred are subgroups in which one of $A_1$ and $A_2$ is phenyl or naphthyl which is unsubstituted or preferably ortho-substituted by halogen, $C_1$–$C_3$alkyl, $C_1$–$C_3$haloalkyl, $C_1$–$C_3$alkoxy, $C_1$–$C_3$haloalkoxy, $C_1$–$C_3$alkylthio, $C_1$–$C_3$alkoxycarbonyl or nitro; and also those in which $A_1$ and/or $A_2$ is the unsubstituted pyridyl radical or the pyridyl radical which is ortho-substituted as indicated above; or is a furanyl or thiophenyl radical which is unsubstituted or preferably ortho-substituted by halogen, cyano, $C_1$–$C_3$alkyl or $C_1$–$C_3$alkoxycarbonyl; or is a pyrimidin-2-yl radical which is unsubstituted or substituted preferably in the 4- or 6-position by halogen, cyano, $C_1$–$C_3$alkyl, $C_1$–$C_3$haloalkyl, $C_1$–$C_3$alkoxy, $C_1$–$C_3$haloalkoxy, mono- or di($C_1$–$C_3$alkyl)amino, or is a symmetrical triazin-2-yl radical.

Preferred individual compounds are:
1-(4-methyl-6-methoxypyrimidinyl-2)-3-[(2'-methoxyphenyl)sulfamoyl]urea,
1-(4,6-dimethoxypyrimidinyl-2)-3-[(2'-methoxycarbonylphenyl)sulfamoyl]urea,
1-(4-methyl-6-methoxypyrimidinyl-2)-3-methyl-3-[(2'-methoxycarbonylphenyl)sulfamoyl]urea,
1-(4-methyl-6-methoxypyrimidinyl-2)-3-[(2',5'-dimethoxyphenyl)sulfamoyl]urea,
1-(4-methyl-6-methoxypyrimidinyl-2)-3-[(2'-methylphenyl)sulfamoyl]urea,
1-(4-methyl-6-methoxypyrimidinyl-2)-3-[(2'-ethylphenyl)sulfamoyl]urea, and
1-(4-methyl-6-methoxypyrimidinyl-2)-3-methyl-3-(phenylsulfamoyl)urea.

The novel triaza compounds of the formula I may be prepared by the following processes:

A first process comprises reacting an amine of the formula II

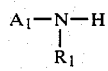   (II)

wherein $A_1$ and $R_1$ have the given meanings, with an isocyanatosulfonyl halide of the formula III $$OCN-SO_2-Hal \quad (III)$$

wherein Hal is a halogen atom, preferably a chlorine atom, in an inert organic solvent or diluent, and then reacting the so obtained sulfamoylhalide urea of the formula IV

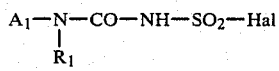   (IV)

wherein A, Hal and $R_1$ are as defined above, if desired without isolating it from the reaction mixture, with an amine of the formula V

   (V)

wherein $A_2$ and $R_3$ are as defined above and, if desired, further reacting the resultant final product with the hydroxide of an alkali metal or alkaline earth metal or with a quaternary ammonium base.

Compounds in which $R_3$ is hydrogen may be prepared as follows: A sulfamoylamide of the formula VI

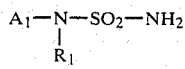   (VI)

wherein $A_1$ and $R_1$ are as defined above, is reacted with an isocyanate of the formula VII $$OCN-A_2 \quad (VII)$$

wherein $A_2$ is as defined above, in an inert solvent or diluent.

If desired, the compounds of formula I may be converted into addition salts with alkali metal hydroxides or alkaline earth metal hydroxides or with quaternary ammonium bases. This is accomplished e.g. by reacting compounds of formula I with an equimolar amount of base and removing the solvent by evaporation.

The above processes are carried out in inert organic solvents, e.g. hydrocarbons such as benzene, toluene, xylene or cyclohexane; chlorinated hydrocarbons such as methylene chloride, chloroform, carbon tetrachloride or chlorobenzene; and ethers such as diethyl ether, dimethoxyethane, diethylene glycol dimethyl ether, tetrahydrofuran or dioxan. Preferred solvents are cyclic or polyvalent ethers such as tetrahydrofuran, dioxan or dimethoxyethane.

The reactions are exothermic. It may therefore be necessary to cool the reaction vessel. The process is carried out in the temperature range from $-70°$ to $+80°$ C., preferbly from $0°$ to $40°$ C.

The starting compounds of the formulae II and III are known and/or may be easily prepared by known methods.

The compounds of the formula I are stable compounds and no precautionary measures are required for handling them. When used in lower rates of application, the compounds of formula I have good selective growth-inhibiting and selective herbicidal properties which make them most suitable for use in crops of useful plants, especially in cereals, cotton, soybeans, maize and rice. In some cases damage is also caused to weeds which have up to now have only been controlled with total herbicides.

The mode of action of these compounds is unusual. Many are translocatable, i.e. they are absorbed by the plant and transported to other parts of it where they then exert their action. Thus, for example, it is possible to damage perennial weeds to their roots by surface treatment.

The compounds of formula I also have pronounced plant growth-regulating, especially plant growth-inhibiting, properties. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops are not able to compete with the cultivated plants.

Further, the compounds of formula I are suitable for preventing stored potatoes from seeding. During winter storage, potatoes often develop sprouts which result in shrinkage, weight loss, and rot.

When the compounds of formula I are applied in higher rates of application, all tested plants are so damaged in their development that they wither and die.

The invention also relates to herbicidal and plant growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosed in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalates or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcum kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepolite or bentonite; and suitable non-sorbent carriers are materials such as calcite or sand. In addition, a great number of preganulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyl laurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp., Ringwodd, N.J., 1979; Sisely and Wood, "Encyclopedia of Surface Active Agents", Chemical Publishing Co. Inc., New York, 1964.

The pesticidal formulations usually contain 0.1 to 95%, preferably 0.1 to 80%, of a compound of the formula I, 1 to 99.9% of a solid or liquid adjuvant, and 0 to 25%, preferably 0.1 to 25%, of a surfactant.

Preferred formulations are composed in particular of the following constituents (%=percentage by weight):

Emulsifiable concentrates active ingredient: 1% to 20%, preferably 5 to 10%
surfactant: 5% to 30%, preferably 10 to 20%
liquid carrier: 50% to 94%, preferably 70 to 85%

Dusts active ingredient: 0.1 to 10%, preferably 0.1 to 1%
solid carrier: 99.9 to 90%, preferably 99.9 to 99%

Suspension concentrates active ingredient: 5 to 75%, preferably 10 to 50%
water: 94 to 25%, preferably 90 to 30%
surfactant: 1 to 40%, preferably 2 to 30%

Wettable powders active ingredient: 0.5 to 90%, preferably 1 to 80%
surfactant: 0.5 to 20%, preferably 1 to 15%
solid carrier: 5 to 95%, preferably 15 to 90%

Granulates active ingredient: 0.5 to 30%, preferably 3 to 15%
solid carrier: 99.5 to 70%, preferably 97 to 85%.

Whereas commercial products will be preferably formulated as concentrates, the end user will normally employ dilute formulations. The formulations can be diluted to a concentration as low as 0.001%. The rates of application are normally 0.01 to 10 kg a.i./ha, preferably 0.025 to 5 kg a.i./ha.

The compositions may also contain further ingredients such as stabilisers, antifoams, viscosity regulators, binders, adhesives, as well as fertilisers or other active compounds, in order to attain special effects.

EXAMPLE 1

(1-(4-Methyl-6-methoxypyrimidin-2-yl)-3-[2'-methoxyphenyl)sulfamoyl]urea

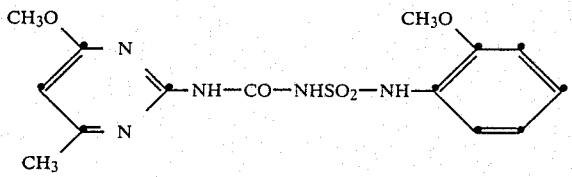

8.3 g (0.06 mole) of 2-amino-4-methoxy-6-methylpyrimidine are dissolved at elevated temperature in 75 ml of dioxan and 75 ml of dimethoxyethane. After cooling to about 5° C., 5.7 ml (0.066 mole) of chlorosulfonyl isocyanate are rapidly added dropwise while keeping the temperature at about 20° C. with an ice-bath. The clear, slightly yellowish solution is then cooled to about 5° C. and 14.9 ml (0.132 mole) of 2-methoxyaniline are added. The ensuing reaction is weakly exothermic and the hydrochloride begins to precipitate. After 30 minutes the reaction mixture is concentrated at 45° C. in a water jet vacuum. The residue is taken up in 250 ml of methylene chloride and the resultant suspension is washed with 150 ml of 2% hydrochloric acid. The clear solution so obtained is dried over magnesium sulfate and filtered over Hyflo after addition of activated carbon. The solvent is stripped off, to give 18 g (82% of theory) of a clear, orange yellow oil which crystallises at room temperature. This crude product may be triturated with a small amount of diethyl ether and filtered. The title compound is obtained as a pale beige coloured product with a melting point of 142°–143° C.

EXAMPLE 2

(1-(4,6-Dimethoxypyrimidin-2-yl)-3-[(2'-methoxycarbonylphenyl)sulfamoyl]urea

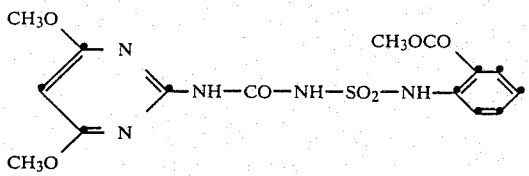

5.5 g (0.036 mole) of 2-amino-4,6-dimethoxypyrimidine are dissolved in 50 ml of methylene chloride and the solution is cooled to 5° C. At this temperature, 3.3 ml (0.0375 mole) of chlorosulfonyl isocyanate are rapidly added dropwise. The intermediate precipitates and 9.7 g (0.075 mole) of methyl anthranilate are added to the beige suspension. The ensuing reaction is slightly exothermic and a clear solution is obtained. However, the already formed hydrochloride precipitates after a few seconds. After it has stood for about 15 minutes at room temperature, the reaction mixture is washed with 100 ml of 2% hydrochloric acid and the organic phase is dried over magnesium sulfate and concentrated, affording the crude product in the form of a clear, yellow oil in quantitative yield. This oil is dissolved in about 50 ml of diethyl ether. Trituration yields 12.5 g (84.5% of theory) of the title compound in the form of white crystals with a melting point of 161°–163° C.

The following compounds are obtained by procedures corresponding to those described in the foregoing Examples:

1-(4-methyl-6-methoxypyrimidinyl-2)-3-methyl-3-[(2'-methoxycarbonylphenyl)sulfamoyl]urea, m.p. 132°–133° C.;

1-(4-methyl-6-methoxypyrimidinyl-2)-3-(N-ethyl-N-phenylsulfamoyl)urea, m.p. 159°–161° C.;

1-(4-methyl-6-methoxypyrimidinyl-2)-3-(2-methoxyphenylsulfamoyl)urea, m.p. 142°–143° C.;

1-(4,6-dimethoxypyrimidinyl-2)-3-(2-chlorophenylsulfamoyl)urea, m.p. 164°–165° C.;

1-(4-methyl-6-methoxypyrimidinyl-2)-3-[(2',5'-dimethoxyphenyl)sulfamoyl]urea, m.p. 140°–141° C.;

1-(4-methyl-6-methoxypyrimidinyl-2)-3-[(2'-ethylphenyl)sulfamoyl]urea, m.p. 133°–134° C.;

1-(4-methyl-6-methoxypyrimidinyl-2)-3-[(2'-methylphenyl)sulfamoyl]urea, m.p. 138°–140° C.;

1-(4-methyl-6-methoxypyrimidinyl-2)-3-methyl-3-(phenylsulfamoyl)urea, m.p. 150°–152° C.;

1-(4,6-dimethoxy-1,3,5-triazinyl-2)-3-methyl-3-[(2'-methoxycarbonylphenyl)sulfamoyl]urea;

1-(4,6-dimethoxy-1,3,5-triazinyl-2)-3-(phenylsulfamoyl)urea;

1-(4,6-dimethoxy-1,3,5-triazinyl-2)-3-[(2'-methoxyphenyl)sulfamoyl]urea;

1-(4,6-dimethoxy-1,3,5-triazinyl-2)-3-[(2'-methylphenyl)sulfamoyl]urea;

1-(4,6-dimethoxy-1,3,5-triazinyl-2)-3-methyl-3-[(2'-methylphenyl)sulfamoyl]urea;

1-(4,6-dimethoxy-1,3,5-triazinyl-2)-3-[(2'-ethylphenyl)sulfamoyl]urea;

1-(4-methyl-6-methoxy-1,3,5-triazinyl-2)-5-methyl-3-(phenylsulfamoyl)urea, m.p. 144°–146° C.;

1-(4-methyl-6-methoxy-1,3,5-triazinyl-2)-3-[(2'-methoxyphenyl)sulfamoyl]urea;

1-(4-methyl-6-methoxy-1,3,5-triazinyl-2)-3-[(2'-methoxycarbonylphenyl)sulfamoyl]urea;

1-(4-methyl-6-methoxy-1,3,5-triazinyl-2)-3-methyl-3-[(2'-methoxycarbonylphenyl)sulfamoyl]urea, m.p. 148°–149° C.;

1-(4-methyl-6-methoxy-1,3,5-triazinyl-2)-3-[(2'-methylphenyl)sulfamoyl]urea;

1-(4-methyl-6-methoxy-1,3,5-triazinyl-2)-3-methyl-3-[(2'-methylphenyl)sulfamoyl]urea;

1-(4-methyl-6-methoxy-1,3,5-triazinyl-2)-3-[(2'-chlorophenyl)sulfamoyl]urea, m.p. 133°–134° C.;

1-(4-methyl-6-methoxy-1,3,5-triazinyl-2)-3-(β-naphthylsulfamoyl)urea;

1-(4,6-dimethoxy-1,3,5-triazinyl-2)-3-(β-naphthylsulfamoyl)urea;

1-(4-methyl-6-methoxypyrimidinyl-2)-3-(β-naphthylsulfamoyl)urea;

1-(4,6-dimethoxypyrimidinyl-2)-3-(β-naphthylsulfamoyl)urea;

1-(4,6-dimethoxypyrimidinyl-2)-3-methyl-3-(phenylsulfamoyl)urea, m.p. 145°–146° C.;

1-(4,6-dimethoxypyrimidinyl-2)-3-(2-cyanophenylsulfamoyl)urea, m.p. 144°–145° C.;

1-(4,6-dimethoxypyrimidinyl-2)-3-(2-trifluoromethylphenylsulfamoyl)urea, m.p. 153°–154° C.;

1-(4,6-dimethoxypyrimidinyl-2)-3-(2,6-dichlorophenylsulfamoyl)urea, m.p. 148°–150° C.;

1-(4,6-dimethoxypyrimidinyl-2)-3-methyl-3-(2-methoxycarbonylphenylsulfamoyl)urea, m.p. 148°–150° C.;

1-(4,6-dimethoxypyrimidinyl-2)-3-(indanyl-1-sulfamoyl)urea, m.p. 191°–192° C.;

1-(4,6-dimethylpyrimidinyl-2)-3-(2-chlorophenylsulfamoyl)urea, m.p. 140°–141° C.;

1-(4-methoxy-6-methylpyrimidinyl-2)-3-(2-chlorobenzylsulfamoyl)urea, m.p. 154°–155° C.

FORMULATION EXAMPLES

EXAMPLE 3

Formulation examples for compounds of formula I (throughout, percentages are by weight)

| (a) Wettable powders | (a) | (b) | (c) |
|---|---|---|---|
| active ingredient | 20% | 60% | 0.5% |
| sodium lignosulfonate | 5% | 5% | 5% |
| sodium laurylsulfate | 3% | — | — |
| sodium diisobutylnaphthalene-sulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| active ingredient | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| active ingredient | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| active ingredient | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| active ingredient | 3% |
| polyethylene glycol 200 | 3% |

| (e) Coated granulate (continued) | |
|---|---|
| kaolin | 94% |

The finely ground active ingredient is uniformly applied, in a mixer, to the kaolin moistened with polyethylene glycol. Non-dusty coated granulates are obtained in this manner.

| (f) Suspensionconcentrate | (a) | (b) |
|---|---|---|
| active ingredient | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| active ingredient | 5% |
| isopropylamine | 1% |
| octylphenol polyethylene glycol ether (78 moles of ethylene oxide) | 3% |
| water | 91% |

BIOLOGICAL EXAMPLES

EXAMPLE 4

Preemergence herbicidal action

In a greenhouse, plant seeds are sown in flower pots of 12–15 cm diameter. Immediately after sowing, the surface of the soil is treated with an aqueous dispersion or solution of the compounds to be tested. Concentrations of 4 kg a.i./ha are employed. The pots are then kept in the greenhouse at 22°–25° C. and 50–70% relative humidity. The test is evaluated 3 weeks later.

The compounds of Examples 1 and 2 exhibit good herbicidal activity in this test.

EXAMPLE 5

Postemergence herbicidal action (contact action)

A number of weeds and cultivated plants in pots, both monocuts and dicots, are sprayed postemergence, in the 4- to 6-leaf stage, with an aqueous active ingredient dispersion at a rate of application of 4 kg a.i./ha, and then kept at 24°–26° C. and 45–60% relative humidity. The test is evaluated 15 days after treatment. In this test too the compounds of Examples 1 and 2 exhibit good herbicidal activity against the test plants.

EXAMPLE 6

Inhibition of sprouting in stored potatoes

A number of commercially available potatoes of the "Urgenta" variety, without sprouts, are washed and dried. The potatoes are then immersed in emulsions of the compounds to be tested in different concentrations, placed on filter paper in plastic dishes, and kept in the dark at 14°–21° C. and 50% relative humidity. Evaluation is made 34 days after application.

The percentage weight loss of the tubers and the weight of the sprouts compared with untreated controls are simultaneously determined. The compounds of formula I inhibit sprouting completely in this test. At the same time, the weight loss of the potatoes was less than 10% of the weight loss of the control potatoes.

EXAMPLE 7

Growth inhibition of tropical cover crops

The test plants (centrosema plumieri and centrosema pubescens) are reared until fully grown and then cut back to a height of 60 cm. The plants are sprayed 7 days later with an aqueous emulsion of the compound to be tested. The test plants are kept at 70% relative humidity and 6000 lux artificial light for 14 hours per day, at day temperatures of 27° C. and night temperatures of 21° C. The test is evaluated 4 weeks after application.

The new growth in comparison with the control is assessed and the phytotoxicity is determined. In this test, new growth of plants treated with compounds of the formula I is markedly reduced (less than 20% of the new growth of untreated controls), without damage being caused to the test plants.

What is claimed is:

1. A compound selected from the group consisting of (i) a sulfamoylurea of the formula

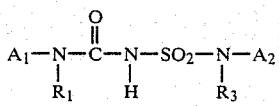

wherein $A_1$ is pyrimidin-2-yl or 1,3,5-triazin-2-yl, each of which is unsubstituted, monosubstituted in the 4-position or disubstituted in the 4- and 6-positions with the same or different substituents selected from the group consisting of halo, cyano, alkyl of 1 to 3 carbon atoms, haloalkyl of 1 to 3 carbon atoms, alkoxy of 1 to 3 carbon atoms, haloalkoxy of 1 to 3 carbon atoms, alkylamino of 1 to 3 carbon atoms and dialkylamino of 1 to 3 carbon atoms in each alkyl group;

$A_2$ is phenyl, naphthyl or indanyl, each of which is unsubstituted or substituted by one or two members selected from the group consisting of halo, alkyl of 1 to 3 carbon atoms, haloalkyl of 1 to 3 carbon atoms, alkoxy of 1 to 3 carbon atoms, haloalkoxy of 1 to 3 carbon atoms, alkylthio of 1 to 3 carbon atoms, alkoxycarbonyl of 1 to 3 carbon atoms in the alkoxy group, and nitro; and each of $R_1$ and $R_3$ independently is hydrogen or alkyl of 1 to 4 carbon atoms; and (ii) the alkali metal, alkaline earth metal and quaternary ammonium salts thereof.

2. A compound according to claim 1 wherein $A_1$ is pyridin-2-yl which is substituted in the 4- position by methyl or methoxy and in the 6- position by methyl or methoxy.

3. A compound according to claim 1 wherein said sulfamoylurea is 1-(4,6-dimethoxypyrimidinyl-2)-3-[(2'-methoxycarbonylphenyl)sulfamoyl]urea.

4. A compound according to claim 1 wherein said sulfamoylurea is 1-(4-methyl-6-methoxypyrimidinyl-2)-3-methyl-3-[(2'-methoxycarbonylphenyl)sulfamoyl]urea.

5. A compound according to claim 1 wherein said sulfamoylurea is 1-(4-methyl-6-methoxypyrimidinyl-2)-3-[(2',5'-dimethoxyphenyl)sulfamoyl]urea.

6. A compound according to claim 1 wherein said sulfamoylurea is 1-(4-methyl-6-methoxypyrimidinyl-2)-3-[(2'-methylphenyl)sulfamoyl]urea.

7. A compound according to claim 1 wherein said sulfamoylurea is 1-(4-methyl-6-methoxypyrimidinyl-2)-3-[(2'-ethylphenyl)sulfamoyl]urea.

8. A compound according to claim 1 wherein said sulfamoylurea is 1-(4-methyl-6-methoxypyrimidinnyl-2)-3-methyl-3-(phenylsulfamoyl)urea.

9. A composition for controlling the growth of unwanted plants which comprises an effective amount of a compound according to claim 1 and a carrier therefore.

10. The method of controlling the growth of unwanted plants which comprises applying to the plants or to the area of their growth an effective amount of a compound according to claim 1.

11. A compound according to claim 1 wherein said sulfamoylurea is 1-(4-methyl-6-methoxypyrimidinyl-2)-3-[(2'-methoxyphenyl)sulfamoyl]urea.

* * * * *